(12) United States Patent
Ungerer et al.

(10) Patent No.: US 10,067,097 B2
(45) Date of Patent: Sep. 4, 2018

(54) METHOD FOR TESTING A WORKPIECE USING ULTRASOUND

(71) Applicant: AREVA GmbH, Erlangen (DE)

(72) Inventors: Dieter Ungerer, Nürnberg (DE); Joachim Ritter, Neunkirchen am Brand (DE); Sebastian Gripp, Alzenau (DE)

(73) Assignee: AREVA GMBH, Erlangen (DE)

( * ) Notice: Subject to any disclaimer, the term of this patent is extended or adjusted under 35 U.S.C. 154(b) by 0 days.

(21) Appl. No.: 15/123,946

(22) PCT Filed: Mar. 5, 2015

(86) PCT No.: PCT/EP2015/054636
§ 371 (c)(1),
(2) Date: Sep. 6, 2016

(87) PCT Pub. No.: WO2015/132343
PCT Pub. Date: Sep. 11, 2015

(65) Prior Publication Data
US 2017/0030869 A1    Feb. 2, 2017

(30) Foreign Application Priority Data

Mar. 7, 2014 (DE) .......................... 10 2014 103 097

(51) Int. Cl.
*G01N 29/275* (2006.01)
*G01N 29/04* (2006.01)
*G01N 29/28* (2006.01)

(52) U.S. Cl.
CPC .......... *G01N 29/275* (2013.01); *G01N 29/04* (2013.01); *G01N 29/28* (2013.01); *G01N 2291/044* (2013.01)

(58) Field of Classification Search
CPC .. G01N 29/275; G01N 29/227; G01N 29/228; G01N 29/28; G01N 29/04;
(Continued)

(56) References Cited

U.S. PATENT DOCUMENTS 3,712,119 A    1/1973    Cross et al.
4,558,598 A *    12/1985    Young .................... G01N 29/28
                                                                                                73/644

(Continued)

FOREIGN PATENT DOCUMENTS

DE    102 59 653 B3    4/2004
DE    10258336 B3    4/2004

(Continued)

OTHER PUBLICATIONS

International Application No. PCT/EP2015/054636 International Preliminary Report on Patentability dated Sep. 15, 2016 (6 Pages).

*Primary Examiner* — Manish S Shah
*Assistant Examiner* — Suman K Nath
(74) *Attorney, Agent, or Firm* — Keller Jolley Preece

(57) ABSTRACT

The invention relates to a method for testing a workpiece using ultrasound, wherein an ultrasonic probe generates an ultrasound signal which has a central beam and which is coupled into the workpiece under test, and the central beam is guided along a predefined path on the surface of the workpiece, the central beam and the workpiece being moved in opposite directions at least along a portion of the path.

7 Claims, 4 Drawing Sheets

(58) Field of Classification Search
CPC ....... G01N 2291/044; G01N 2291/101; G01N 2291/106; G01N 2291/263; G01N 2291/2632; G01N 2291/2634; G01N 29/265; G01N 29/27
USPC .................................. 73/621, 633, 642, 644
See application file for complete search history.

(56) References Cited

U.S. PATENT DOCUMENTS

| | | |
|---|---|---|
| 5,373,743 A | 12/1994 | Abrahams |
| 2004/0020298 A1 | 2/2004 | Siverling et al. |
| 2009/0120189 A1 | 5/2009 | Fei et al. |
| 2009/0126496 A1* | 5/2009 | Maurer .................. G01N 29/28 73/644 |

FOREIGN PATENT DOCUMENTS

| | | |
|---|---|---|
| DE | 10 2005 041 971 A1 | 3/2007 |
| WO | 2012/062343 A1 | 5/2012 |

* cited by examiner

METHOD FOR TESTING A WORKPIECE USING ULTRASOUND

CROSS-REFERENCE TO RELATED APPLICATIONS

This application is a national phase entry under 35 U.S.C. § 371 of International Application No. PCT/EP2015/054636, filed Mar. 5, 2015, which claims the benefit of German Application No. 10 2014 103 097.4, filed Mar. 7, 2014. The entire contents of each of the foregoing patent applications are hereby incorporated by reference.

BACKGROUND OF THE INVENTION

1. Field of the Invention

The invention relates to a method for testing a workpiece using ultrasound. In order to test workpieces in a non-destructive manner using ultrasound, it is known to generate an ultrasound signal by means of an ultrasonic test head, said ultrasound signal being coupled into the workpiece under test either directly via air or by means of a liquid jet, such as a water jet for example, along a prespecified path on the surface of the workpiece. In the case of this so-called squirter technique, a liquid jet is formed by means of a nozzle and is then directed onto the surface of the workpiece. In order to couple-in the ultrasound along the prespecified path, the liquid jet is moved owing to a corresponding movement of the nozzle. The nozzle is moved for this purpose over the stationary workpiece, for example by means of a large mobile portal, synchronized linear shafts or other devices with the same purpose as a test fork, also called yoke.

2. Background and Relevant Art

The test mechanism provides a position for the position of the squirter nozzle. Test mechanisms can be portals with extension arms, linear shaft systems or else robots. The tool center point represents the point at which the jet strikes the component under test. This point is defined by the 3-dimensional position of the squirter nozzle and the distance from the component.

It is also possible for a plurality of squirter nozzles to be used in parallel.

In order to achieve the greatest possible productivity, the acceleration and the final speed of the movement along the path have to be selected to be as high as possible, so that a test period which is as short as possible is achieved. However, the liquid jet is deflected at the same time owing to mass inertia and air resistance. This is all the more severe the higher the acceleration and final speed are selected to be. This deflection has an adverse effect on the test result. In extreme cases, the test becomes unusable if the deflection of the liquid jet becomes too severe.

US 2009/120189 A1, U.S. Pat. No. 3,712,119 A and WO 2012/062343 A1 disclose conventional ultrasound testing methods in which the ultrasound signal is coupled into the workpiece by means of a direct contact or a coupling medium. The workpiece moves in relation to an ultrasonic transducer during the ultrasound testing operation.

U.S. Pat. No. 5,373,743 discloses a method for testing a workpiece, in which an ultrasound signal is coupled into a workpiece by means of a liquid jet. The liquid jet is guided along a path over the surface of the workpiece.

BRIEF SUMMARY OF THE INVENTION

The object of the present invention is therefore to specify a method for testing a workpiece using ultrasound, in which the above problems are avoided.

According to the invention, this object is achieved by an ultrasound signal which has a central beam is generated by an ultrasonic test head, which ultrasound signal is coupled into the workpiece under test along a prespecified path on the surface of the workpiece by means of at least one liquid jet, and in which the central beam is guided along a prespecified path on the surface of the workpiece, wherein the central beam and the workpiece are moved in opposing directions at least on a portion of the path, for example the component moves to the right and the central beam moves to the left.

In this case, the central beam ideally represents the ultrasound signal as a linear illustration. Therefore, the origin of this central beam is in the ultrasonic test head and said central beam strikes a point on the surface of the workpiece. The central beam runs along the prespecified path on the surface of the workpiece for the purpose of testing the workpiece.

An opposing movement of the workpiece and central beam means a simultaneous movement of the workpiece and the central beam in an opposite direction. In this case, the speeds of the respective movements can have different values, but are preferably identical.

The ultrasound signal is coupled into the workpiece by means of at least one liquid jet. Therefore, a simultaneous movement of the liquid jet along the prespecified path also takes place with the central beam. The movement of the workpiece in the opposing direction to the movement direction of the liquid jet on its own does not influence the deflection of the liquid jet. Therefore, the opposing movements result, overall, in an addition firstly of the speed of the workpiece and secondly of the speed of the moving liquid jet to form an overall test speed, but with only the speed of the liquid jet being critical for the deflection of said liquid jet. The opposing or counter-directional movement of the workpiece and the water jet therefore allows a considerable increase in the acceleration and final speed of form an overall test speed and therefore the productivity, with the test quality increasing at the same time. This also applies, in particular, for curved workpieces.

The liquid jet used can have, for example, a round cross section which is generated by a pinhole aperture, or an elongate cross section which is generated by an elongate groove.

Higher overall test speeds are achieved, in particular in the case of a meandering manner of movement, that is to say a movement of the workpiece and the liquid jet along a meandering path, with a reversal in the movement directions and the subsequent acceleration phase by combining the movements of the liquid jet and the workpiece. However, a higher overall test speed is also possible at a constant test speed, with simultaneous workpiece movement in the opposite direction to the movement of the liquid jet. This results in a higher productivity, with the test quality increasing at the same time. The points at which the liquid strikes the workpiece and the tool center point differ from one another to a lesser extent owing to the reduced deflection, for example said influences from air resistance and mass inertia, and therefore distortion of the liquid jet. Smaller deviations of the workpiece position and the tool center point of the test mechanism are achieved. The increase in the jet pressure generates a "more powerful" jet which is influenced to a lesser extent but, owing to the geometry and design of the squirter nozzle, eddying which causes interference when water flows through occurs, said eddying in turn influencing the test result in which the signal sensitivity drops. The accuracy of fault determination on the workpiece (position and size) increases considerably.

More accurate true positioning over the component is achieved. Therefore, rapid changes in direction can be removed at the end of a, for example, horizontal path in the case of a meandering manner of movement. Therefore, a change in direction does not necessarily have to take place outside the workpiece, but rather can take place within the workpiece at the workpiece end.

In a preferred refinement of the invention, the workpiece is tested by means of a pulse-echo technique. This means that there has to be at least one ultrasonic test head and at least one nozzle for the liquid jet only on one side of the workpiece. In this case, the ultrasonic test head serves as a transceiver device.

As an alternative, ultrasound can also be passed through the workpiece, which means that ultrasonic test heads and nozzles for forming a liquid jet are arranged on both sides with respect to the workpiece. An ultrasonic test head for emitting the ultrasound signal is located on one side of the workpiece, and an ultrasonic test head for receiving the ultrasound signal is located on the opposite side of the workpiece.

An opposing movement of the central beam or liquid jet and the workpiece can also take place in a multi-dimensional manner, so that the above-described advantages apply to all dimensions and the geometry of complicated workpieces can also be tested in an efficient manner.

The movement of the central beam or liquid jet in the opposing direction in relation to the workpiece can preferably take place owing to a translatory movement or else owing to a pivoting movement of the ultrasonic test head or of the nozzle which forms the water jet.

In a preferred refinement of the invention, the opposing movement of the workpiece and the central beam or liquid jet takes place on a portion of the path in an end region of the workpiece. The movement of the workpiece and the liquid jet can then take place in a conventional manner on further portions of the path. However, the opposing movement can also extend over the entire workpiece under test.

BRIEF DESCRIPTION OF THE DRAWINGS

Reference is made to the exemplary embodiments of the drawing for further explanation of the invention, in which, in each case in a schematic basic outline.

DETAILED DESCRIPTION

Figure 1:
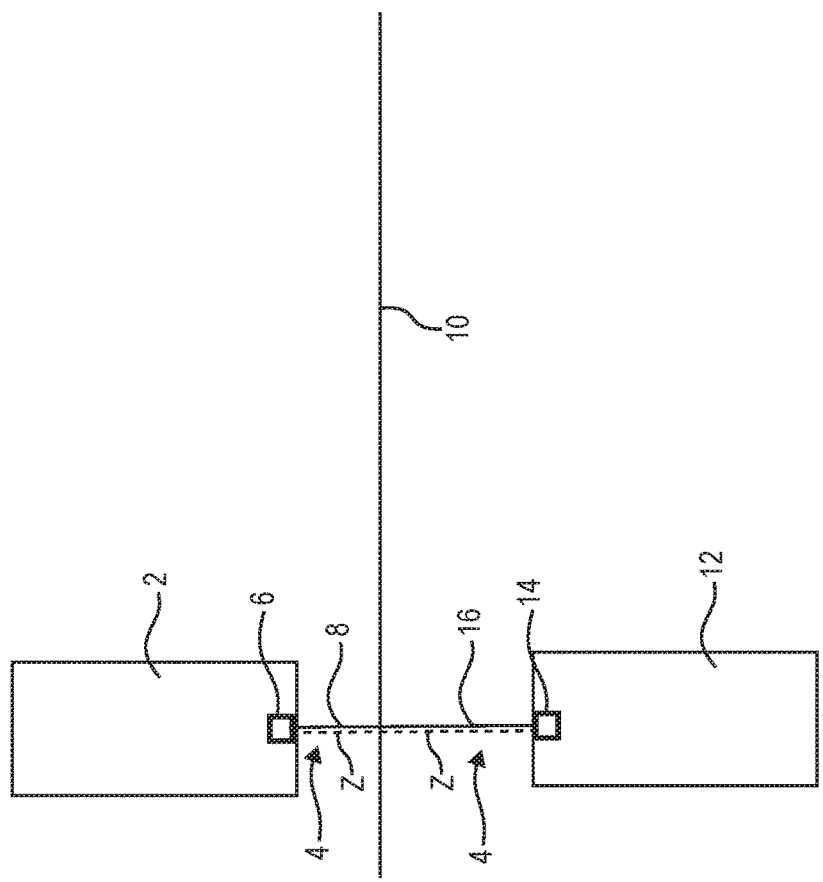
FIG. 1 shows a lateral cross-sectional view of a test arrangement for testing the material of a workpiece in a non-destructive manner.

FIG. 1 shows an apparatus for testing material in a non-destructive manner, which apparatus comprises a first ultrasonic test head 2 for generating an ultrasound signal 4 which has a central beam (Z). A nozzle 6 with which a liquid jet 8 is formed is also arranged on the ultrasonic test head 2. The ultrasound signal 4 is coupled into a workpiece 10, which in this case constitutes a flat panel, by means of the liquid jet 8. However, workpieces 10 of virtually any desired other geometries can also be tested by the test arrangement shown in FIG. 1.

A second ultrasonic test head 12 is arranged on that side of the workpiece 10 which is situated opposite the first ultrasonic test head 2, which second ultrasonic test head likewise comprises a nozzle 14 with which a liquid jet 16 is formed, said liquid jet likewise being directed onto the workpiece and with which the ultrasound signal 4 is routed to the ultrasonic test head 12 after said ultrasonic test head has passed ultrasound through the workpiece 10, so that said ultrasound signal can be received by the ultrasonic test head 12. The respective distances of the ultrasonic test heads 2, and also of the nozzles 6, 14 from the workpiece 10 are preferably identical, but can also be different.

Figure 2:
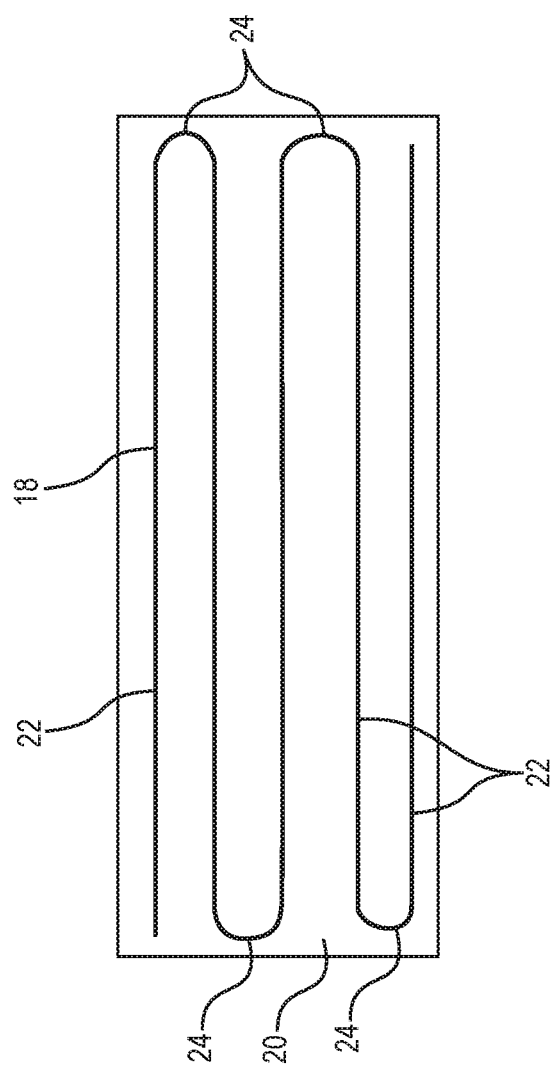
FIG. 2 shows a plan view of the workpiece from FIG. 1 with a prespecified path along which the workpiece is tested.

In order to achieve sufficient test coverage of the workpiece 10, the test takes place along a prespecified path 18 on the surface 20 of the workpiece 10, it being necessary for the ultrasound signal 4 to be coupled into the workpiece 10 along said prespecified path. The central beam (Z) is therefore guided along this path 18 in order to test the workpiece 10. A path 18 of this kind is illustrated in greater detail in FIG. 2. Said path is a meandering two-dimensional path which has a plurality of rows 22 and reversal points 24. However, it would also be possible to couple the ultrasound signal 4 into the workpiece 10 along a three-dimensional path 18 using the method according to the invention. In this case, the path 18 runs in an arcuate manner in the region of the reversal points 24. However, all other forms are also possible, such as angular or zigzag forms for example. Here, the regions of the reversal points 24 are situated on the surface of the workpiece 10. However, they can also be situated outside the workpiece 10.

Figure 3:
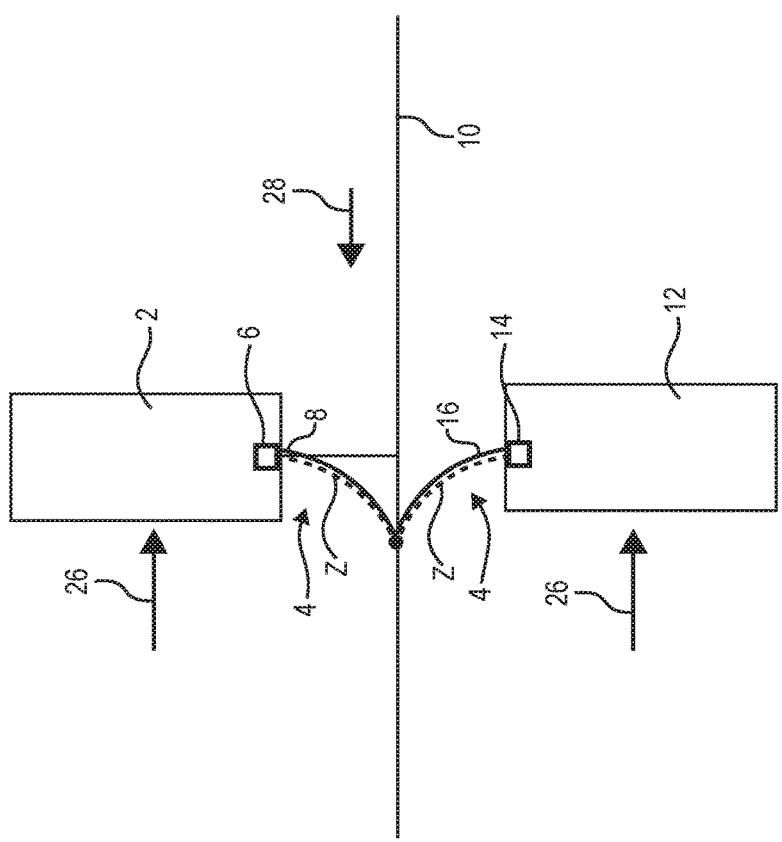
FIG. 3 shows the test arrangement from FIG. 1 during a test situation.

The workpiece 10 is then tested in the following manner, as is illustrated in greater detail in FIG. 3. In order to couple the ultrasound signal 4 into the workpiece 10 under test along the path 18, the central beam Z and the liquid jets 8, 16 and the workpiece 10 are moved in opposing directions at least on a portion of the path 18. In order, for example, to run along a row 22 of the path 18, the central beam Z and the liquid jets 8 and 16 are moved in the direction of the arrows 26, as a result of which the liquid jets 8 and, respectively, 16 are deflected in the opposite direction, for example owing to the mass inertia. At the same time, the workpiece 10 is moved in the opposite direction, that is to say in the direction of the arrow 28. Shortly before reaching a reversal point 24, the workpiece 10 and the liquid jets 8, 16 are braked and move along the path 18 on a further row 22. A further test is then performed along the next row 22 with opposing movements of the workpiece 10 and the liquid jets 8, 16 in directions which are each opposite to arrows 26, 28. The respective movement of the liquid jets 8, 16 is generated by a translatory movement of the corresponding nozzles 6, 14 in the same direction. The distance of the tool center point from the point at which the jet strikes is dependent on the acceleration forces which occur, and should ideally turn out to be as small as possible. A small deflection improves the test quality. A large deflection obviously results in a further disadvantage. The point at which the jet strikes is located next to the tool center point which relates to a squirter position of the mechanism. Specifically in these particular cases, the detected echo signal is assigned to another position. Specifically when repositioning an indicator, it is clear from the workpiece 10, since in this case the squirter nozzle 6, 14 is stationary in one location and the liquid jet 8, 16 does not undergo any deflection, that the fault is only partial or is not apparent at all in this position. Therefore, the fault position is not the same as the squirter position in this case.

This is obvious, in particular, in a region around the reversal point 24.

Therefore, a lower movement speed of the nozzle 6, 14 is advantageous. A movement speed of the squirter nozzle 6, 14 is usually intended to be set equal to the squirter test speed.

Particularly in the case of a movement of this kind of the workpiece 10 and the central beam Z or liquid jets 8, 16 along a meandering path 18, higher overall test speeds are achieved with a reversal of the movement directions and the subsequent acceleration phase by combining the movements of liquid jets 8, 16 and the workpiece 10. However, a higher overall test speed is also possible at a constant test speed with simultaneous workpiece movement in the opposite direction to the movement of the liquid jets 8, 16. The overall test speed is given, specifically, by adding the individual values of the speeds of the workpiece 10 and liquid jets 8, 16. However, the value of the speed of the liquid jets 8, 16 or central beam Z does not necessarily have to be equal to the speed of the workpiece in this case.

This procedure is advantageous particularly in the case of 3-dimensional workpiece geometries. However, this may also be advantageous in the case of a high workpiece mass with the accompanying moments of mass inertia since the workpiece 10 can be moved to a high workpiece speed only after moderate acceleration.

Figure 4:
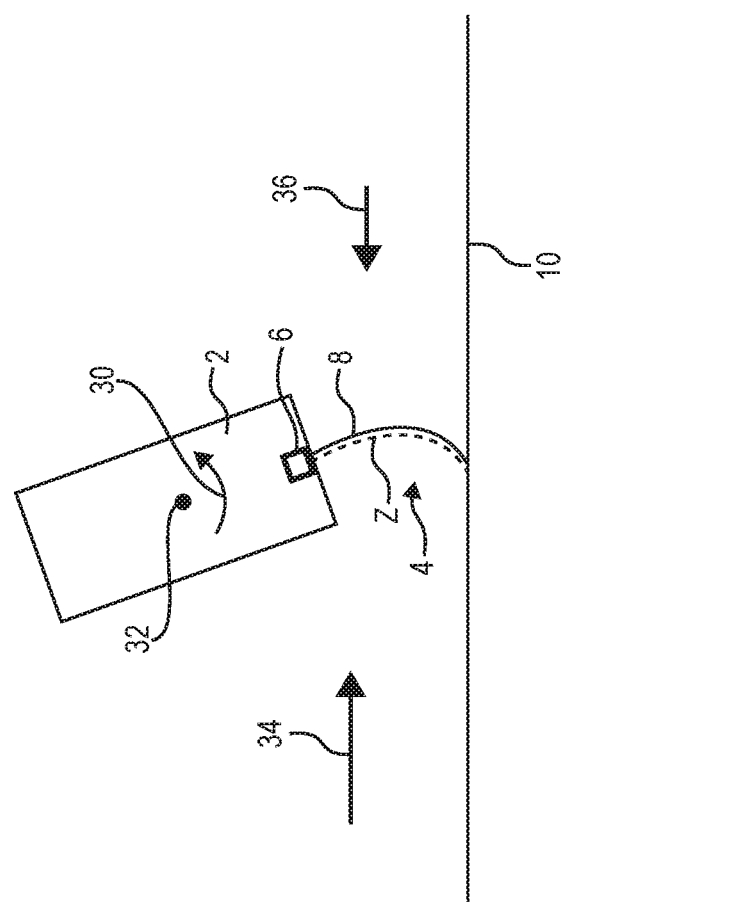
FIG. 4 shows the test arrangement from FIG. 1 during a further test situation.

A further embodiment of the invention is illustrated in FIG. 4, in which the workpiece 10 is tested by means of a pulse-echo technique. This means that there is only a single ultrasonic test head 2 which generates an ultrasound signal 4 which is coupled into the workpiece 10 by means of a liquid jet 8 which is formed by a nozzle 6. The echo of the ultrasound signal 4, which echo is generated by the workpiece 10, is likewise received by the ultrasonic test head 2. A movement of the central beam Z or of the liquid jet 8 is additionally achieved here, for example by means of a pivoting or rotational movement of the ultrasonic test head 2 or of the nozzle 6 in the direction of the arrow 30 around the fulcrum 32, so that the central beam Z or liquid jet 8 moves in the direction of the arrow 34 in relation to the workpiece 10, and the workpiece 10 itself is moved in the direction of the arrow 36. Depending on the direction of movement, the ultrasonic test head 2 can be adjusted in or opposite to the direction of the arrow 30. Wagging of the test head in this way, with the change in orientation of the test head 2 to the workpiece 10, may be advantageous in the case of short test tracks. The different types of movement of the individual nozzles 6, 14 are not tied to the ultrasonic test technique in this case, but rather can be combined as desired. In a particular case, two ultrasonic test heads which are situated opposite one another can be used when ultrasound is passed through.

LIST OF REFERENCE SYMBOLS

2 Ultrasonic test head
4 Ultrasound signal
6 Nozzle
8 Liquid jet
10 Workpiece
12 Ultrasonic test head
14 Nozzle
16 Liquid jet
18 Path
20 Surface
22 Row
24 Reversal point
26 Arrow
28 Arrow
30 Arrow
32 Fulcrum
34 Arrow
36 Arrow
Z Central beam

The invention claimed is:

1. A method for testing a workpiece using ultrasound, in which an ultrasound signal which has a central beam is generated by an ultrasonic test head, which ultrasound signal is coupled into the workpiece under test by means of at least one liquid jet, and the central beam is guided along a prespecified path on the surface of the workpiece together with the at least one liquid jet, comprising:
   moving the ultrasonic test head together with the at least one liquid jet in a first multidimensional direction; and
   moving the workpiece in a second multidimensional direction;
   wherein the first multidimensional direction and the second multidimensional direction are opposite to each other along a portion of the prespecified path and moving the workpiece and the ultrasonic test head occur simultaneously.

2. The method as claimed in claim 1, in which the workpiece is tested by means of a pulse-echo technique.

3. The method as claimed in claim 1, in which ultrasound is passed through the workpiece at least once.

4. The method as claimed in claim 1, in which a movement of the central beam takes place owing to a translatory movement of the ultrasonic test head.

5. The method as claimed in claim 1, in which a movement of the central beam takes place owing to a pivoting movement of the ultrasonic test head.

6. The method as claimed in claim 1, in which the opposing movement takes place on a portion of the path in an end region of the workpiece.

7. The method as claimed in claim 1, in which the opposing movement extends over the entire workpiece under test.

* * * * *